(12) United States Patent
Her

(10) Patent No.: US 6,545,754 B2
(45) Date of Patent: Apr. 8, 2003

(54) POST-SEAL INSPECTION SYSTEM AND METHOD

(75) Inventor: Tay Bok Her, Melaka (MY)

(73) Assignee: Asti Holdings, Limited, Kallang Basin Industrial Estate (SG)

( * ) Notice: Subject to any disclaimer, the term of this patent is extended or adjusted under 35 U.S.C. 154(b) by 0 days.

(21) Appl. No.: 10/096,181

(22) Filed: Mar. 11, 2002

(65) Prior Publication Data

US 2002/0105637 A1 Aug. 8, 2002

Related U.S. Application Data

(63) Continuation of application No. 09/814,022, filed on Mar. 21, 2001, now Pat. No. 6,396,578, which is a continuation of application No. 09/429,824, filed on Oct. 29, 1999, now Pat. No. 6,259,522.

(30) Foreign Application Priority Data

Jul. 10, 1999 (ML) .......................................... PI9902923

(51) Int. Cl.$^7$ .......................... G01N 21/00; B65D 85/30
(52) U.S. Cl. .................... 356/237.5; 206/713; 206/714; 382/145; 348/126
(58) Field of Search ................................ 206/713, 714, 206/715–717, 710, 701; 209/577, 586; 356/237.1–237.5, 394; 29/833, 593, 740, 743, 742; 382/145, 147, 151, 293; 348/126

(56) References Cited

U.S. PATENT DOCUMENTS

| | | | |
|---|---|---|---|
| 4,028,728 A | | 6/1977 | Sharp .......................... 358/106 |
| 4,894,790 A | | 1/1990 | Yotsuya et al. ................. 382/8 |
| 5,191,470 A | * | 3/1993 | Wickholm et al. ........... 359/375 |
| 5,667,073 A | | 9/1997 | Okui ........................... 206/713 |
| 6,055,054 A | * | 4/2000 | Beaty et al. .............. 356/237.1 |
| 6,084,663 A | * | 7/2000 | Seng ........................ 356/237.4 |
| 6,102,210 A | | 8/2000 | Mikami ....................... 206/714 |

FOREIGN PATENT DOCUMENTS

| | | |
|---|---|---|
| JP | 9-236487 | 9/1997 |
| JP | 2000-275032 | 10/2000 |
| JP | 2001-18911 | 1/2001 |

* cited by examiner

*Primary Examiner*—Hoa Q. Pham
(74) *Attorney, Agent, or Firm*—Christopher J. Rourk; Akin Gump Strauss Hauer & Feld, LLP

(57) ABSTRACT

A system for inspection components that are sealed within tape is provided. The system includes a light source that can illuminate the components through a tape layer. A polarizer is used to polarize light from the light source, the components, and the tape layer, so as to reduce glare and reflected light. An image system receives light from the polarizer and stores image data for each component.

12 Claims, 6 Drawing Sheets

POST-SEAL INSPECTION SYSTEM AND METHOD

This application is a Continuation application of application Ser. No. 09/814,022, now U.S. Pat. No. 6,396,578 filled Mar. 21, 2001 which was a continuation of application Ser. No. 09/429,824, filed on Oct. 29, 1999, which issued as U.S. Pat. No. 6,259,522, issued Jul. 10, 2001.

FIELD OF THE INVENTION

The present invention relates to inspection systems, such as those used to inspect surface mount type semiconductor devices, and more particularly to systems and methods for inspection of components through sealing or cover tape after the components have been sealed with the tape.

BACKGROUND OF THE INVENTION

Unintended deformation of semiconductor devices may be a well-known problem in the semiconductor industry. This problem has been addressed by inspecting semiconductor devices and components both before (pre-seal) and after (post-seal) the devices or components are packaged for shipping. Existing methods for performing post seal inspection require the use of an operator to perform 100 percent inspection, because of variability in the sealing tape used for immobilizing semiconductor devices and components.

The current process used by most manufacturers is to do an automated vision inspection at pre-seal and a post seal gross manual inspection. The post seal gross manual inspection involves examining the devices with the human eye through a magnifying glass. Although doing a manual post seal inspection is better than doing no post seal inspection at all, the manual post seal inspection is very time consuming and not very cost effective and therefore not very efficient. In addition, as more and more semiconductor processes become automated, a manual post seal inspection becomes less desirable.

No automated method has been developed that can examine the semiconductor devices for defects after the devices have packaged for shipping. The problem has been the ability to generate a clear and detailed image of the semiconductor device when such device is disposed beneath a layer of sealing or cover tape. The sealing or cover tape layer causes extreme light scattering and light reflection, which can severely distort the image of the device beneath the tape. Because of this image distortion caused by the sealing or cover tape layer, the practice in the field has been to merely do a manual post seal inspection of devices packaged under sealing or cover tape.

Although it is desirable to automate all inspection processes for semiconductor devices and components, many physical obstacles have prevented an automated post seal inspection system for devices and components disposed beneath the sealing or cover tape. The glossy cover tape causes light reflection and light dispersion, which creates noise when a camera is trying to produce an image of the device. The cover tape is not very translucent so the clarity of the device disposed beneath the tape is impaired. Also, the cover or sealing tape has anti-static coating as well as filler particles that worsen visibility through the cover or sealing tape. Finally, the inside and outside surfaces of the cover or sealing tape are not perfectly parallel which creates a prism and cause the device disposed beneath to appear distorted.

SUMMARY OF THE INVENTION

This invention provides a system and method relating to an automated vision inspection system in which there may be a system configured to store image data and perform analysis on such image data of a component disposed beneath a tape layer. The image data is captured by shining a light source on the component and then filtering both the incident and reflected light to reduce light reflection and scattering effects in the image data. In addition, the cover or sealing tape layer is stretched to remove surface unevenness in the tape layer. Finally, the components are put as close as possible to the cover or sealing tape layer to increase visibility of the component disposed beneath the tape.

In accordance with another aspect of the present invention, the automated post seal vision inspection system can be coupled to a packing media transfer system or taping/de-taping machine to facilitate in the removal found to be unacceptable during the automated post seal vision inspection.

The technical advance represented by the invention, as well as the objects thereof, will become apparent from the following description of a preferred embodiment of the invention when considered in conjunction with the accompanying drawings, and the novel features set forth in the appended claims.

DETAILED DESCRIPTION OF PREFERRED EMBODIMENTS

Figure 1:
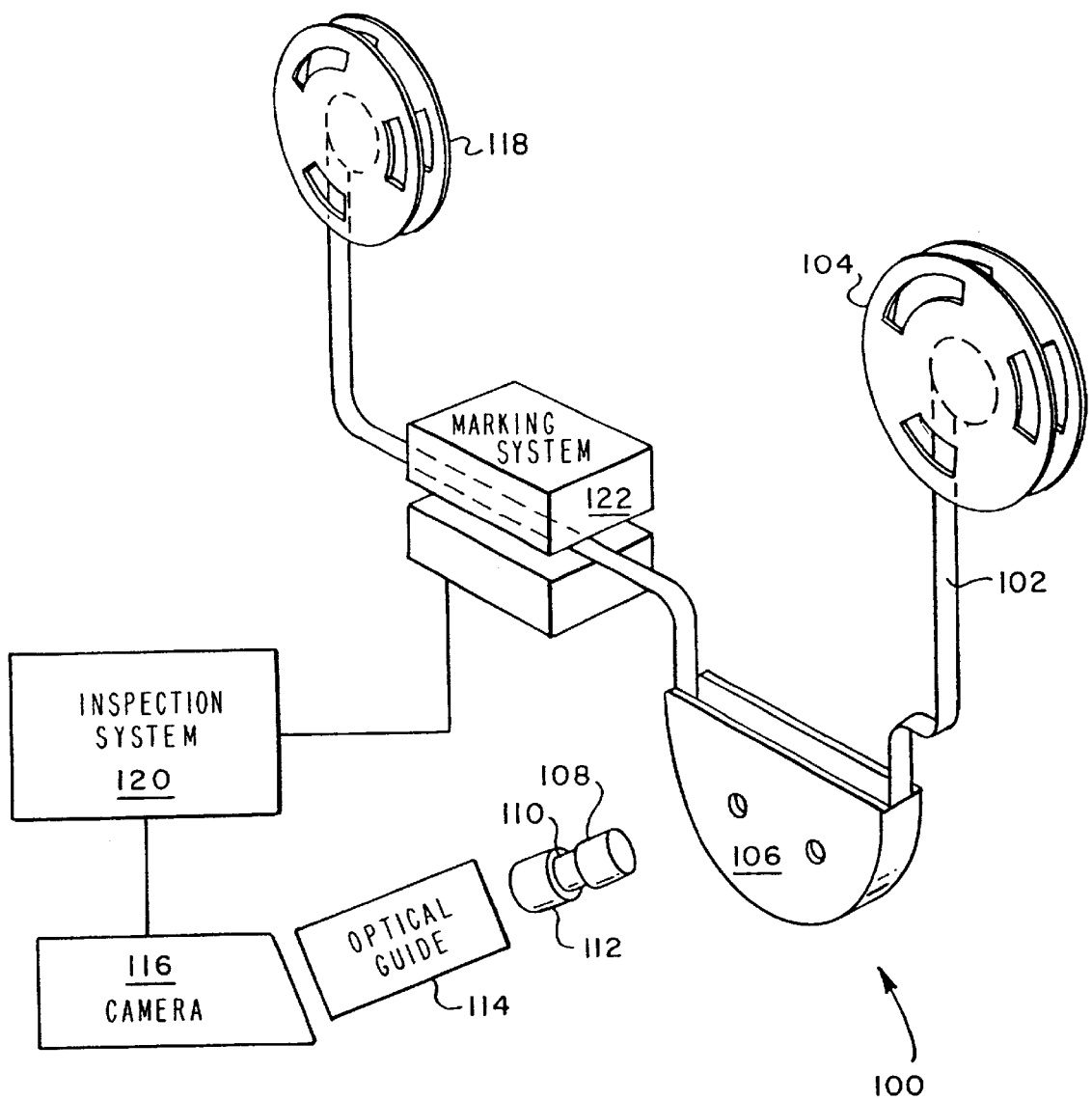
FIG. 1 illustrates an overall view of a post-seal inspection system in accordance with an exemplary embodiment of the present invention.

In the description which follows, like parts are marked throughout the specification and drawing with the same reference numerals, respectively. The drawing figures may not be to scale and certain components may be shown in generalized or schematic form and identified by commercial designations in the interest of clarity and conciseness.

FIG. 1 is a diagram of a post seal inspection system 100 in accordance with an exemplary embodiment of the present invention. Post seal inspection system 100 allows components to be inspected after they have been sealed in packing tape, thus allowing the defective components to be readily detected and corrective measures to be taken before components are shipped to the ultimate user.

Post seal inspection system 100 includes tape 102 and stretching and inversion mechanism 106. Tape 102 may be an embossed polymer tape with a bottom embossed layer and a top sealing layer, wherein the top sealing layer is sealed with adhesive, vacuum, heat or other suitable methods. Other suitable tape sealing mechanisms may also be used. Stretching and inversion mechanism 106 is used to invert tape 102 such that the embossed pocket portion of tape 102 is on top and the sealing portion of tape 102 is underneath. This configuration allows gravity to force the component to lay flush against the sealing tape, thereby enabling automatic optical inspection of the component through the sealing layer of tape 102.

Post seal inspection system 100 includes feeder reel 104 and take-up reel 118. Feeder reel 114 may contain components that have been sealed in tape 102. Tape 102 is fed into stretching and inversion mechanism 106 and is then fed into take-up reel 118. Feeder reel 114 and take-up reel 118 operate in a coordinated manner such that the speed of the tape 102 is controllable through the stretching and inversion mechanism 106.

In addition to inverting tape 102, the stretching and inversion mechanism 106 also stretches tape 102 by forcing tape 102 through a semi-circular path. The stretching effect of the semi-circular path of the stretching and inversion mechanism 106 helps to insure that the sealing portion of tape 102 will present a uniform surface for inspection of the components while the inversion effect insures that the components sealed in tape 102 will be placed against the sealing portion of tape 102. Although a single element is used in this exemplary embodiment to invert and stretch the tape, a system for inverting the tape may be used that is separate from the system for stretching the tape, such as a series of rollers and gears.

Post seal inspection system 100 includes camera 116, which is coupled through optical wave guide 114 to light source 110 and polarizers 108 and 112. Light source 110 generates light that is focused on the components and tape 102. This light is transmitted through polarizing filters 108 and 112 and back through the optical wave guide 114 to camera 116. Light source 110 and polarizers 108 and 112 may be located at the location shown in FIG. 1, which is approximately at a 45 degree angle from vertical, or may alternatively be located at other suitable locations.

Light source 110 may be a light emitting diode array, a filament light array, or other suitable lighting arrays. Light source 110 may be a controlled light source, which generates a predetermined light pattern on tape 102 at a predetermined spot on the stretching and inversion mechanism 106.

The light generated by light source 110 is transmitted first through polarizer 108. Polarizer 108 may be configured to be adjustable by an operator, and may be a polarizing element that is configured to polarize light that is transmitted from light source 110 to tape 102. The light reflects off tape 102 and the components contained therein, and is transmitted back through polarizer 108 and then through polarizer 112. Polarizer 112 may be a polarizing element that may be configured to be adjustable by an operator so as to compensate for reflections generated by the surface of the sealing layer of tape 102.

In one exemplary embodiment, light that is transmitted directly through the sealing layer of tape 102 will be oriented in the same phase as the light emitted by the light source, but light that is scattered by tape 102 or otherwise reflected off a discontinuity in tape 102 will have a different phase. Polarizer 108 thus provides plane-polarized light to illuminate the components sealed in tape 102. Polarizers 108 and 112 may be configured to be controllably adjusted so as to transmit the greatest amount of light that has not been reflected off discontinuities or otherwise scattered by tape 102. Alternatively, light source 110 may be configured to generate phase-oriented light, such as laser light, and polarizers 108 and 112 may be set to provide an optimum level of transmission of non-reflected light.

Optical wave guide 114 may be a suitable optical channel, and may be a nondistorting optical guide such as high precision mirrors. Camera 116 is configured to receive the image generated by light source 110 through optical wave guide 114. Camera 116 may be a charge coupled device, an optical sensor array, or other suitable digital camera that is operable to capture and store image data, such as a 512× 1024 pixel image. Camera 116 may process black and white image data, color image data, or other suitable image data.

Camera 116 is coupled to inspection system 120. Inspection system 120 may be implemented in hardware, software or a suitable combination of hardware and software, and may be an inspection platform with programmable software systems. In one exemplary embodiment, inspection system 120 may be a WAV1000 System manufactured by Semiconductor Technologies and Instruments of Richardson, Tex. Inspection system 120 receives digital image data from camera 116 and performs predetermined analysis functions on the image data. In another exemplary embodiment, inspection system 120 may compare referenced image pixel data to test image pixel data to determine whether the pixel data is within predetermined acceptable ranges. Inspection system 120 may also receive user entered template data to facilitate the setup and testing of components stored within tape 102.

Inspection system 120 is coupled to marking system 122. Marking system 122 is operable to mark components that are determined to be non-standard by inspection system 120. For example, marking system may record an index number on the tape 102 that corresponds with the location of the suspect device. Marking system 122 may also physically mark the tape or use other suitable methods to indicate or record the location of a suspect device.

In operation, tape 102 is inverted and stretched by the stretching and inversion mechanism 106 to facilitate optical testing after sealing. An image of each component sealed within tape 102 is generated by camera 116, which receives calibrated image data from light source 110, polarizer 108, and polarizer 112. Inspection system 120 is configured to process the image data to determine whether the component sealed in tape 102 meets predetermined criteria for acceptability.

Figure 2:
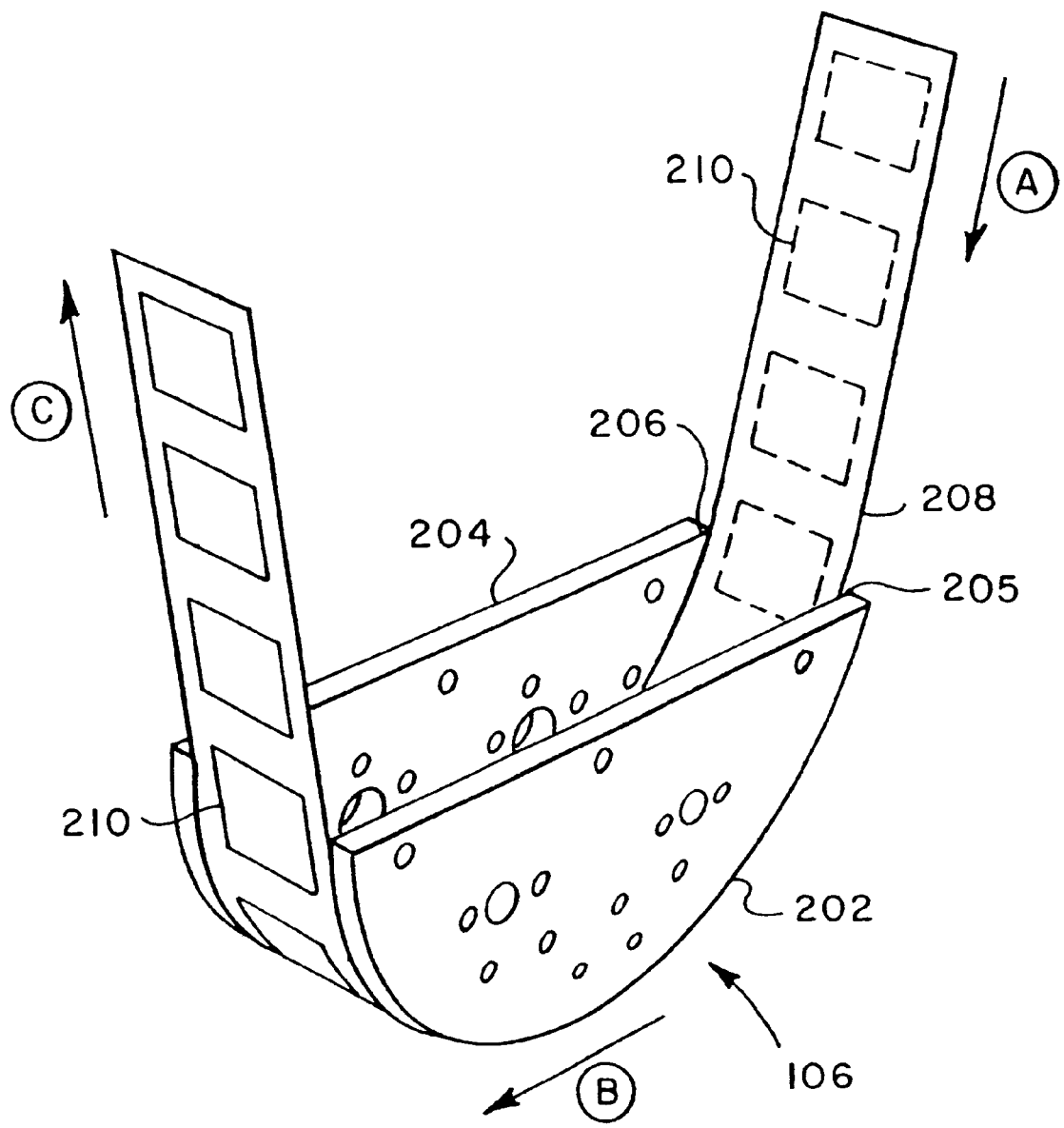
FIG. 2 is a detailed and expanded diagram of a tape stretching and inversion mechanism in accordance with an exemplary embodiment of the present invention.

FIG. 2 is a diagram of a tape stretching and inversion mechanism 106 in accordance with an exemplary embodiment of the present invention. Tape stretching and inversion mechanism 106 may be used to ensure that the sealed components contained within sealing tape are properly oriented prior to performing the post-seal inspection.

Tape stretching and inversion mechanism 106 includes semi-circular component 202 and 204, which are each made of metallic materials, composite materials, or other suitable materials. Semi-circular component 202 includes track 205 and semi-circular component 204 includes track 206. Tracks 205 and 206 are used to control the path taken by tape 208 as it passes through the stretching and inversion mechanism 106. Tape 208 leaves a suitable feeder mechanism, such as feeder reel 104 of FIG. 1, and enters the stretching and inversion mechanism 106 in the direction indicated by arrow "A." After tape 208 enters the stretching and inversion mechanism 106, tape 208 follows the semi-circular tracks 205 and 206 and moves past the area indicated by arrow "B," and then moves out of the stretching and inversion mechanism 106 at the location indicated by arrow "C." Tape 208 is then collected on a suitable collection mechanism, such as take-up reel 118.

Tape 208 is disposed around components 210, which are inspected while tape 208 is being inverted and stretched by tape stretching and inversion mechanism 106. Tape 208 with components 210 enters the stretching and inversion mechanism 106, and the components 210 fall onto the sealing layer of tape 208 by the force of gravity at or before the location shown by arrow "B." In addition, the sealing layer of tape 208 is stretched along the semicircular tracks 205 and 206 of tape stretching and inversion mechanism 106. Thus, the components disposed within tape 208 are placed in a position that is relatively uniform at the location shown by arrow "B," namely, flush against the sealing layer of tape and with the sealing layer of tape stretched taught. This configuration allows a suitable system to obtain digital images of the components disposed within tape 208, and to also obtain a digital image of the seal of tape 208 in the area near the component.

After the tape 208 has been stretched and inverted by stretching and inversion mechanism 106, it may be collected by a suitable collection mechanism. Also or alternatively, tape 208 may be processed by a detaping system, if the post-seal inspection of the tape 208 indicates that a damaged component or improper seal has been identified. An operator may also or alternatively be notified when a damaged component or improper seal has been identified, so that the operator may perform additional analyses of the sealed component to determine whether a need exists to remove or reseal the component.

Figure 3:
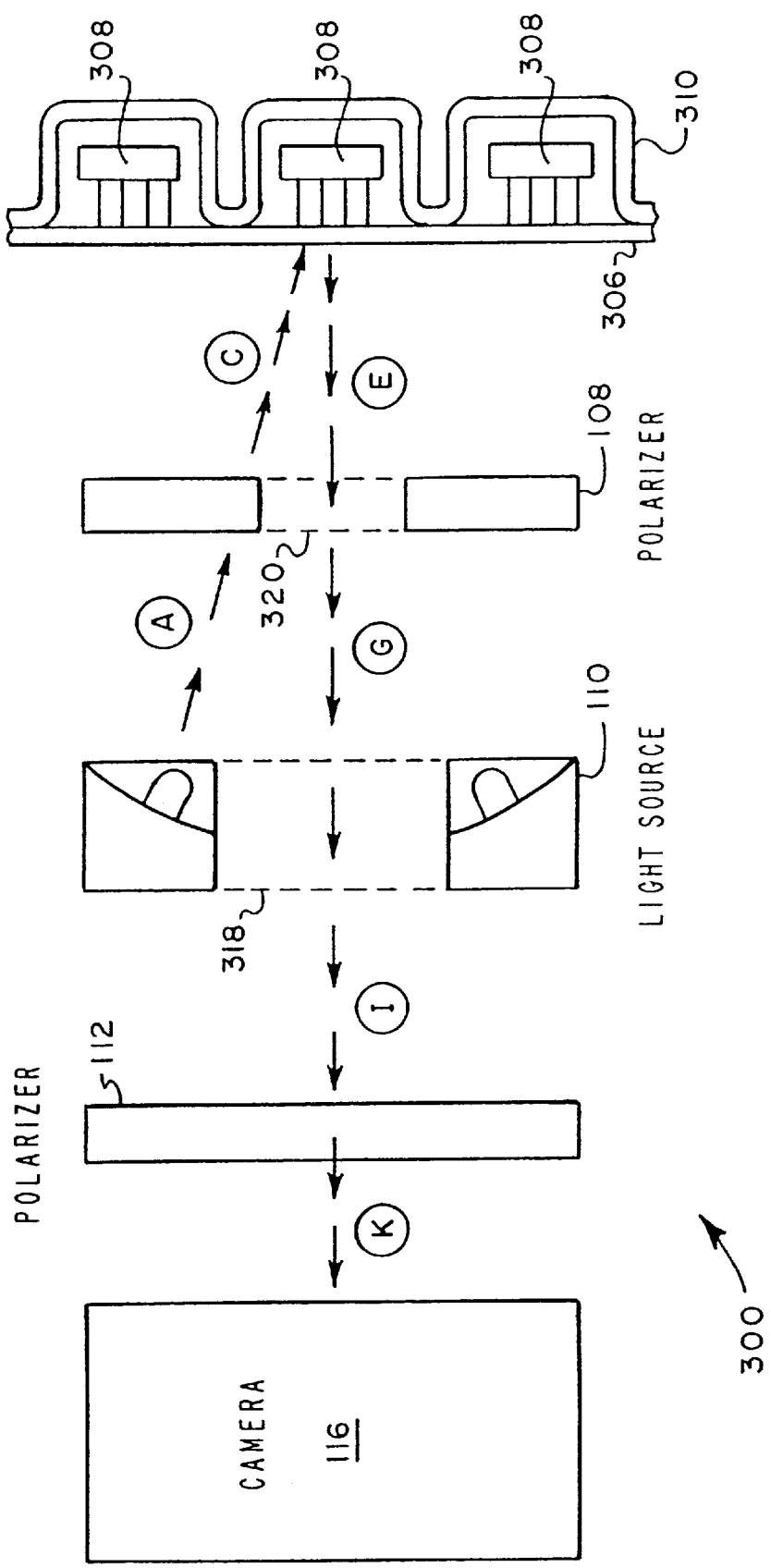
FIG. 3 is a detailed and expanded diagram of a light source and polarizer system in accordance with an exemplary embodiment of the present invention.

FIG. 3 is a diagram of a light source and polarizer system 300 in accordance with an exemplary embodiment of the present invention. Light source and polarizer system 300 is used to generate an image of a component that is disposed beneath a tape layer that may be electronically recorded and analyzed to detect seal and component irregularities.

Light source 110 may be an array of light-emitting diodes or other suitable light sources that generate light having a controllable pattern and intensity. Light source 110 emits light in the direction shown by arrow "A," such that the light passes through polarizer 108. Polarizer 108 is a polarizing element that causes the light emitted by light source 110 to become polarized. In one exemplary embodiment, polarizer 108 is a transparent material that transmits light photons in which the electric vector of the light electromagnetic radiation is oriented in a predetermined plane, and blocks light photons in which the electric vector is oriented in a plane that is orthogonal to the transmission plane. In this manner, all light generated by light source 110 that passes through polarizer 108 will be plane-polarized.

The plane-polarized light follows the path shown by arrow "C" and partially passes through, is partially scattered by, and is partially reflected off of sealing tape layer 306. The plane polarized light illuminates component 308, which rests in embossed carrier tape 310. The plane-polarized light is then emitted from component 308, and passes back through sealing tape layer 306 in the direction of arrow "E." The light travelling in the direction of arrow "E" therefore includes plane polarized light that has been emitted from component 308, plane-polarized light that has been reflected off of sealing tape layer 306, plane polarized light that has been scattered by sealing tape layer 306, and other incident light that been reflected off of component 308 and sealing tape layer 306.

The light travelling in the direction of arrow "E" then passes through aperture 320 of polarizer 108. The light continues in the direction shown by arrow "G" through aperture 318 of light source 110. The light then travels in the direction of arrow "I" through polarizer 112.

Polarizer 112 is a polarizing element. In one exemplary embodiment, polarizer 112 is a transparent material that transmits light photons in which the electric vector of the light electromagnetic radiation is oriented in a predetermined plane, and blocks light photons in which the electric vector is oriented in a plane that is orthogonal to the transmission plane. Polarizer 112 may be adjusted by an operator to function an analyzer, so as to further eliminate light scattering which may have been caused by shining light from light source 110 onto component 308 through sealing tape layer 306. Light travelling in the direction of arrow "K" exits polarizer 112, and is intercepted by camera 116.

Camera 116 is an electro-optical device that may be used to create a digitally-encoded image. Camera 116 may include a predetermined number of picture elements, or pixels, that are operable to receive light or other electromagnetic radiation having a predetermined frequency range. Each picture element may generate a digital value that is representative of the intensity of light being received by that picture element at a point in time. Camera 116 is operable to store such picture element data in a coordinated manner, so that an image may be generated using the picture element data.

In operation, light source and polarizer system 300 is used to generate and store digital image data of a component that is disposed beneath a transparent tape layer. The component is initially oriented in a manner that causes the component to be placed flush against a sealing layer of tape. The sealing layer is also stretched taught, to provide further assurance that the component is in a known location and to reduce the amount of distortion, scattering, and glare that may be created by the sealing tape layer. A light source is then used to illuminate the component, and polarizing elements are used to eliminate glare and other reflected light so as to allow a camera to generate a digital image of the component that has not been distorted, obscured, or otherwise rendered unusable. The digital image may then be analyzed to determine whether the component has been damaged or inadvertently packaged, based upon predetermined data.

Figure 4A:
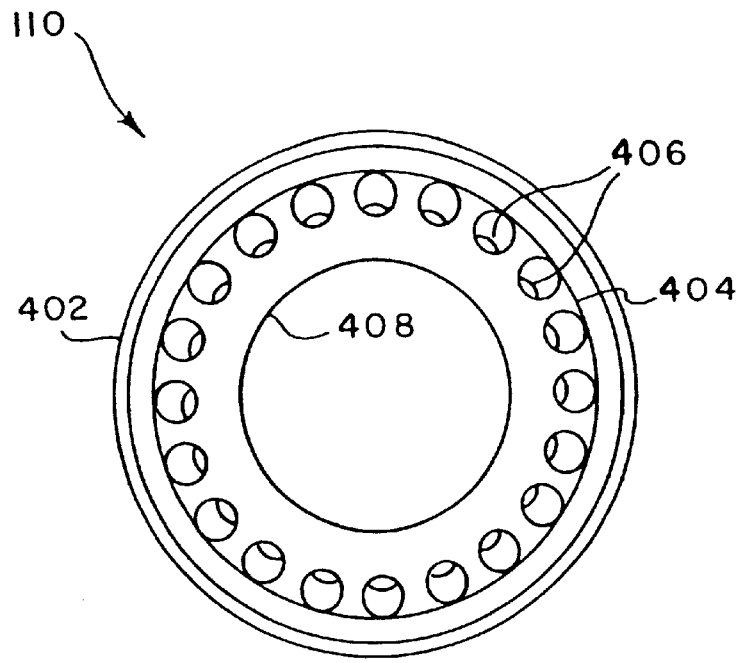
FIG. 4A is a plan view of a light source in accordance with an exemplary embodiment of the present invention.
Figure 4B:
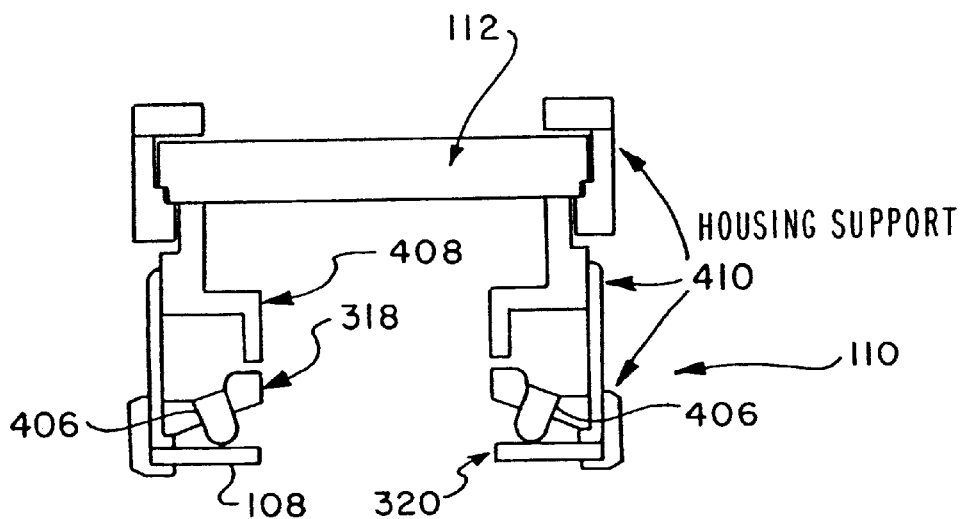
FIG. 4B is a section view of FIG. 4A showing further details of the light source in accordance with an exemplary embodiment of the present invention.

FIG. 4A is a plan view of light source 110 in accordance with an exemplary embodiment of the present invention. FIG. 4B is a section view showing further details of light source 110, polarizer 108, and polarizer 112, as they may be contained within an exemplary housing support 410.

Light source 110 is composed of a suitable support 402, which may be configured in the form of a generally circular ring. Support 402 includes an aperture 408. Aperture 408 allows for the viewing of the component and the capturing of the image of the component by the vision engine, and further allows reflected light to pass back through light source 110 and other components without altering the image data or creating additional light or glare.

Light source 110 may one or more circular arrays 404 of light emitting elements 406. Alternatively, other shapes or arrangements may be used, such as squares, ellipsoids, or other suitable arrangements. The light emitting elements 406 of light source 110 may be light emitting diodes, incandescent light element, fluorescent light elements, or other suitable light elements.

FIG. 4B shows a housing support 410 that holds light source 110, polarizer 108, and polarizer 112. The light emitting elements 406 of light source 110 are held in proximity of polarizer 108. Aperture 320 of polarizer 108 allows polarized light that has been emitted by components 308 to be passed through without additional polarization. The light also passes through aperture 318 of light source 110 and aperture 408 of housing support 410, and is filtered by polarizer 112. Polarizer 112 is adjustable within housing support 410, such that polarizer 112 may be adjusted to compensate for the amount of scattered light that is received from tape 102.

In operation, light emitted from light source 110 is passed through polarizer 108 and illuminates a component 308 that is disposed beneath a sealing tape layer 306. The component 308 emits polarized light, and the sealing tape layer 306 emits reflected and scattered polarized light. A second polarizer 112 may be adjusted within a housing support 410 to block a suitable level of the reflected and scattered polarized light, while allowing a sufficient amount of polarized light to pass to form an image in a camera or other suitable device. In this manner, components that have been sealed within a layer of tape may be inspected for damage, anomalies, non-conformities, or other unacceptable conditions.

Figure 5:
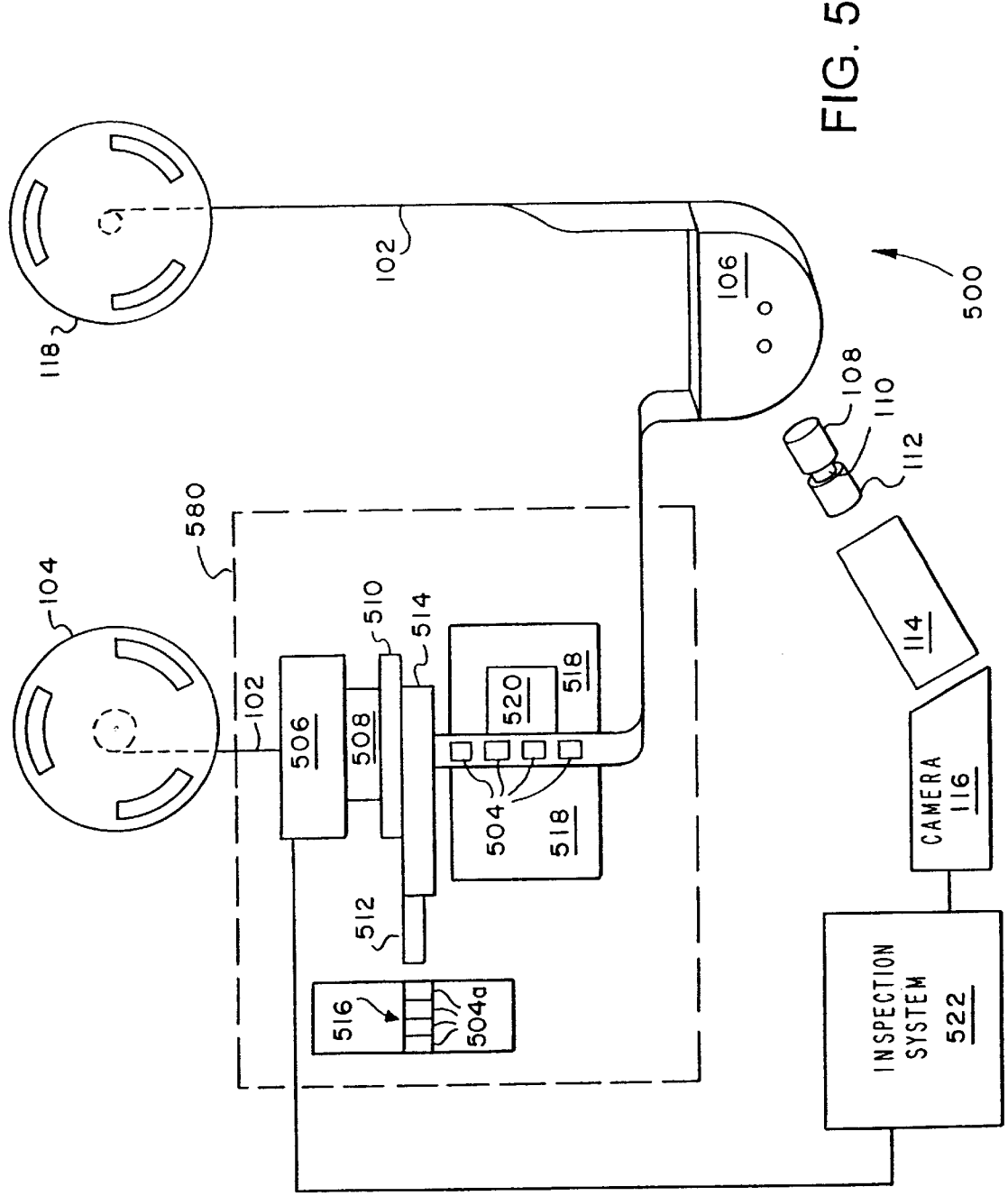
FIG. 5 is a diagram showing a post-seal inspection system coupled to a packing media transfer system in accordance with an exemplary embodiment of the present invention.

FIG. 5 is a diagram of a packing system 500 that includes a post seal inspection system 100, in accordance with an exemplary embodiment of the present invention. Packing system 500 allows components to be removed from packing tape in an automated process if such components are determined to be defective by post seal inspection system Packing system 500 includes tape 102, which leaves feeder reel 104 and receives components 504 at a tape/detape system 580. Tape 102 comprises two components prior to receiving components 504, namely, an embossed portion and a sealing layer. As tape 102 is fed into packing system 500, it is held by supports 508 while a pick and place head 512 of a robot arm 514 is used to pick up components 504a from a packing tube 516. Device handling controller 506 is used to control the advancing of tape 102, and also controls the operation of pick and place head 512, using control arm supports 508 and 510.

After components 504 are placed on the embossed layer of tape 102, the sealing layer of tape 102 is sealed over the embossed layer using a suitable sealing mechanism, such as vacuum, heat, or pressure, so that the components are immobilized within tape 102. Tape 102 is then transferred to stretching and inversion mechanism 106, where it is illuminated by light source and polarizer system 300 as shown in FIG. 3. If a defective component is detected by inspection system 522, then feeder reel 104 and take-up reel 118, and other suitable feeding mechanisms are reversed, such that 102 is taken up on feeder reel 104 and fed by take-up reel 118. In this mode of operation, tape 102 is detaped by tape/detape mechanism 520, and components 504 are removed from tape 102 until all defective components have been removed. The feeder reel 104 and take-up reel 118 may then be reversed to their original direction, such that components may be taped an inspected as required.

Figure 6:
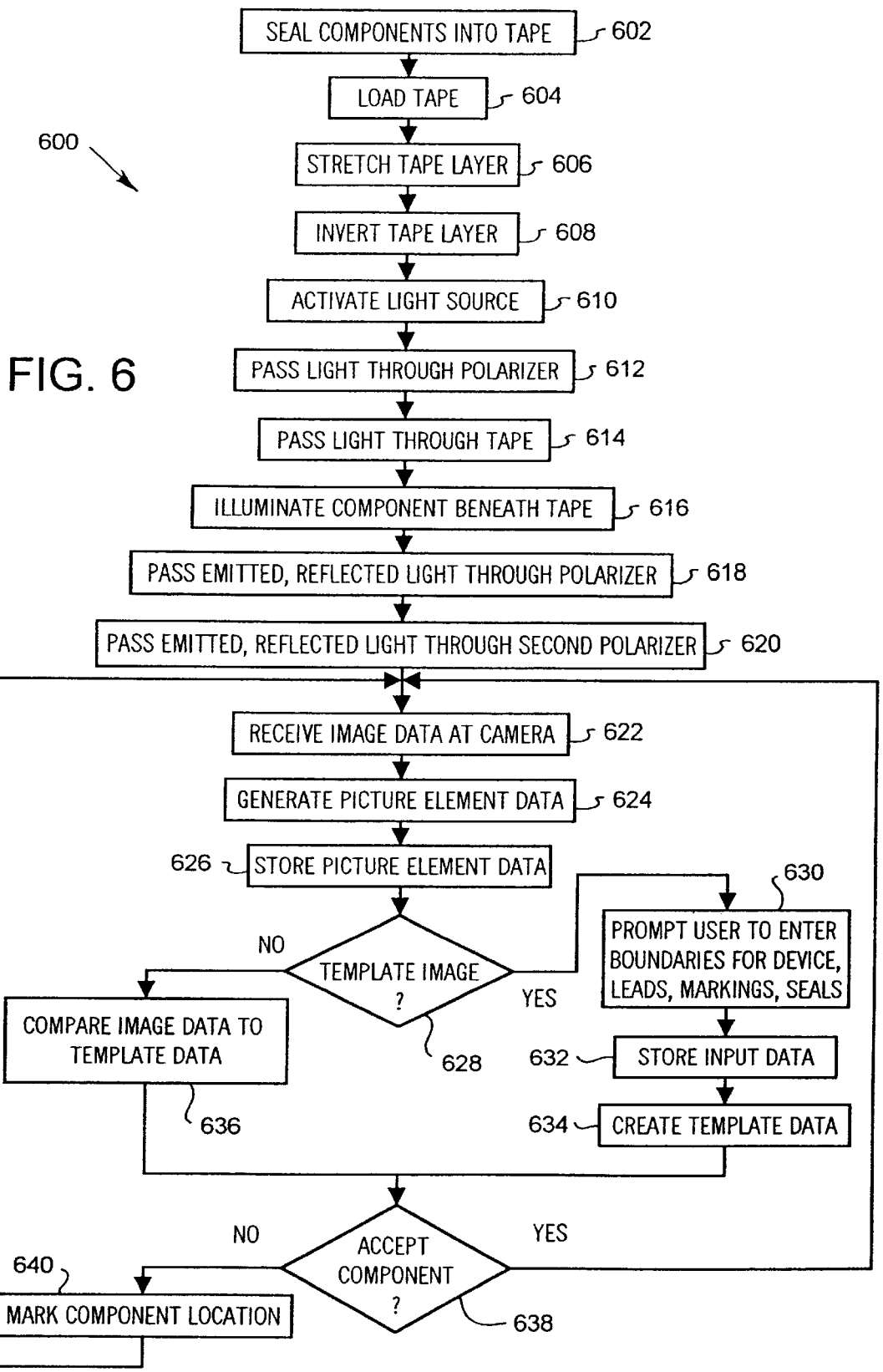
FIG. 6 is a flowchart of a method of operation for a post-seal inspection system in accordance with an exemplary embodiment of the present invention.

FIG. 6 is a flowchart of a method 600 for inspecting components after they have been sealed in a packing material, in accordance with an exemplary embodiment of the present invention. Method 600 may be used to inspect components that have been sealed beneath a tape layer to determine whether such components have been damaged or improperly selected for sealing.

Method 600 begins at 602, where components are packed and sealed within an embossed carrier tape layer and sealing tape layer. The components may be placed in an embossed compartment of a carrier tape while a cover or sealing tape is placed on top of the carrier tape, after which the two tape layers are sealed together using a suitable mechanism, such as a vacuum, heat, or pressure, such that the component is disposed between the embossed carrier tape and the sealing tape layer. The method then proceeds to 604, where the sealed tape containing the components is transferred to the inspection system, such as by directly feeding the sealed tape into the inspection system, by loading the sealed tape onto a reel, or by other suitable methods. The method then proceeds to 606.

At 606, the tape enters a stretching and inversion mechanism, in which the sealing tape layer is stretched in a manner that removes any surface unevenness. The method then proceeds to 608, where the tape layer is inverted to both minimize the distance between the components and the sealing tape layer, and to ensure that the components are in a uniform location relative to the sealing tape. Light is then emitted from a light source at 610, and passes through a polarizer at 612 so as to allow the component to be illuminated with planar polarized light. The method then proceeds to 614.

At 614, the planar polarized light passes through the sealing tape layer, where it falls incident upon the component. At 616, light is reflected and emitted from the tape and the component disposed beneath the tape. This light passes back through the first polarizer at 618, which may include an aperture that allows the light to pass through without polarization at this stage. The image light then passes through the second polarizer at 620, which may be adjustable so as to remove scattered polarized light from the tape sealing layer covering the component, and is received by the camera at 622. The method then proceeds to 624, where image data is generated by the camera. The image data is then transferred to a data storage device, such as a random access memory, a magnetic memory, or other suitable data storage device.

After the image is stored as pixels in a data storage device, the method proceeds to 628 where it is determined whether the image data will be used to create template data. If template data will be created, then the method proceeds to 630 where a user is prompted to select boundaries for the leads, markings, seals, component dimensions within the packaging, and other suitable template data. In one exemplary embodiment, a graphical user interface is provided that allows the user to select coordinates of the template image and to specify boundary lines that should pass through the selected coordinates. For example, the user may select one point in the template image, and may then specify that a circular boundary should pass through this point. The user may then alter the size and location of the circle by "clicking and dragging" the circle. The method then proceeds to 632, where the user-entered data is used to generate a template for the inspection of components. The method then returns to step 622.

If it is determined at step 628 that template data is not required, the method proceeds to step 636. At step 636, the picture element data values are used to determine whether any features of the inspected component exceed allowable tolerances defined in the template. The method then proceeds to step 638 where it is determined whether to accept or reject the component. In one exemplary embodiment, a component will be accepted or rejected based upon whether the picture element data for that component correlates with picture element data for the template. For example, the user-selected template data may define an allowable range for features of the component being inspected. The range selected for the leads, edges, and markings of the device may define an allowable area within which picture elements for any given lead, edge, or marking may be found. Likewise, the template image or a composite template image may be used to compare with the tested component on a pixel-by-pixel basis. If the number of pixels in which a difference in pixel data is observed exceeds a predetermined allowable number of pixels, then the component may be rejected. Likewise, if the absolute magnitude difference in the pixel data exceeds a predetermined allowable difference for a predetermined number of pixels, then the component may be rejected. Furthermore, rather than automatically rejecting the component, the method may include notifying an operator of a suspect component. The operator may then review the image data and decide whether to investigate further.

If it is determined at 638 that the component should not be accepted, then the method proceeds to 640. At 640, the component location is marked by a suitable method, such as by recording an index value, by physically marking the tape, or by other suitable methods. The component may also or alternatively be removed at step 640, such as by a taping-detaping mechanism. The method then returns to step 622 where image data for the next component is obtained.

In operation, components are inspected after they are sealed in tape. The tape is first inverted, such that the components are forced to lie flat on the sealing tape layer by action of gravity. The sealing tape layer is also stretched, to ensure that the surface of the sealing tape layer is flat and creates minimal distortion. Light from a known light source is then used to illuminate the component. The light is polarized to help eliminate distortions that may be caused by reflections or other similar lighting anomalies.

Although preferred and exemplary embodiments of a system for inspecting components that have been sealed in a packing material have been described in detail herein, those skilled in the art will also recognize that various substitutions and modifications may be made to the systems and methods without departing from the scope and spirit of the appended claims.

What is claimed is:

1. A system for inspecting components sealed between a top tape layer and a bottom tape layer comprising:

a light source illuminating the components through a tape layer;

an image processing system capturing and storing image data of the components through the top tape layer; and wherein the components are not affixed to the tape layer.

2. The system of claim 1 further comprising a tape stretching system stretching the top tape layer.

3. The system of claim 1 wherein the image processing system further comprises a polarizer polarizing light from the components.

4. The system of claim 1 wherein the tape stretching system further comprises a tape inversion system.

5. A method for inspecting components comprising:

placing each component on a bottom tape layer;

sealing each component between the bottom tape layer and a top tape layer;

capturing an image of each component through the top tape layer;

generating image data of each component; and
wherein the components are not affixed to either tape layer.

6. The method of claim 5 further comprising stretching the top tape layer prior to capturing the image of each component through the top tape layer.

7. The method of claim 5 further comprising inverting the top tape layer prior to capturing the image of each component through the top tape layer.

8. The method of claim 7 wherein filtering reflected light from each component comprises:

filtering light using a first polarizer before illuminating the component; and filtering reflected light using a second polarizer.

9. The method of claim 5 further comprising:

stretching the top tape layer prior to capturing the image of each component through the top tape layer; and inverting the top tape layer prior to capturing the image of each component through the top tape layer.

10. The method of claim 5 wherein capturing an image of each component further comprises filtering reflected light from each component.

11. The method of claim 7 wherein filtering reflected light from each component comprises filtering incident light and filtering reflected light.

12. The method of claim 7 wherein filtering reflected light from each component comprises filtering reflected light using a polarizer.

\* \* \* \* \*